United States Patent [19]
Fishman

[11] Patent Number: 5,271,401
[45] Date of Patent: Dec. 21, 1993

[54] RADIOLOGICAL IMAGING METHOD

[75] Inventor: Royce S. Fishman, Hillsdale, N.J.

[73] Assignee: Praxair Technology, Inc., Danbury, Conn.

[21] Appl. No.: 820,734

[22] Filed: Jan. 15, 1992

[51] Int. Cl.$^5$ .............................................. A61B 6/00
[52] U.S. Cl. ............................... 128/654; 128/653.4; 128/716; 424/9
[58] Field of Search ..................... 128/653.4, 654, 716, 128/719; 424/9; 436/173

[56] References Cited

U.S. PATENT DOCUMENTS

| | | | |
|---|---|---|---|
| 3,527,205 | 9/1970 | Jones | 128/719 |
| 4,718,432 | 1/1988 | Kimura et al. | 128/654 |
| 4,793,358 | 12/1988 | Kimura et al. | 128/654 |
| 4,939,757 | 7/1990 | Nambu | 378/8 |
| 5,024,230 | 6/1991 | Lindstrom et al. | 128/654 |
| 5,046,498 | 9/1991 | Fishman | 128/653 CA |
| 5,123,414 | 6/1992 | Unger | 128/654 |
| 5,205,290 | 4/1993 | Unger | 128/654 X |

FOREIGN PATENT DOCUMENTS 47692 9/1988 Japan.

OTHER PUBLICATIONS

Evaluation of xenon as a gaseous roentgenographic contrast material, Rockoff, et al., Review of Respiratory Disease, 86, 434–438, 1962.
Use of Xenon Inhalation for Contrast Enhancement, Zilkha, et al., Journal of Neurology, 41, 370–373, 1978.
Experimental Xenon Enhancement with CT Imaging, Drayer, et al., AJR, 44, 134–139, 1980.
Local Lung Ventilation Using Nonradioactive Xenon–Enhanced Transmission Computed Tomography, Snyder, et al., CCM, 12, 46–51, 1984.
Stable Xenon CT/CBF Imaging, Yonas, et al., 1987.
Xenon Enhanced Computed Tomography, Herbert, et al., JCAR, 6, 1088–1093, 1982.

Primary Examiner—Lee S. Cohen
Assistant Examiner—Brian L. Casler
Attorney, Agent, or Firm—Stanley Ktorides

[57] ABSTRACT

A radiological imaging method employing a contrast enhancement agent comprising stable xenon, oxygen and helium, for use with computerized two and three dimensional X-Ray systems and software used with said systems, in the imaging and quantitative measurement of pulmonary ventilation, patency of, distribution of and gas flow in the trachea, bronchi, bronchioles and alveoli, evaluation and optimization of respiratory therapy gas mixtures and pressures separately and in combination, liver blood flow, renal blood flow, cerebral blood flow and brain tissue function.

13 Claims, 2 Drawing Sheets

RADIOLOGICAL IMAGING METHOD

TECHNICAL FIELD

This invention relates generally to radiological imaging and more specifically to a method of contrast enhancement that improves the capability of X-Ray based computerized radiological technology to image and quantitatively measure the physiology of the tracheal-bronchial-alveolar respiratory gas spaces, the pulmonary ventilation process, liver blood flow, renal blood flow, cerebral blood flow and brain tissue function.

BACKGROUND ART

Radiological imaging includes the use of X-Rays or radiopharmaceuticals to produce an image, and/or qualitatively and/or to quantitatively determine the functionality of, for example, a specific compartment such as the bronchi in the lungs, or organ such as the lungs, or organ system such as the pulmonary encompassing the tracheal-bronchial-alveoli gas spaces, pulmonary arterio-venous system, and soft lung tissue.

Radiological imaging using X-Rays includes computerized and non-computerized imaging equipment. It is a definite trend in radiology for X-Ray based imaging technology to be computerized, allowing for software driven new imaging techniques, digital storage of files, and evaluation or manipulation of the basic stored data at some time after the original study, all of which improve the benefits that can be derived from the patient's exposure to radiation. Examples of three dimensional technologies include but are not limited to computerized tomography (CT), high speed computerized tomography, high resolution computerized tomography, and software based three dimensional reconstruction and helical, spiral and volumetric continuous scanning which allows a CT to produce a three dimensional image of for example the lungs or heart which can be viewed from any angle aspect and/or any depth. Examples of two dimensional technologies include digital radiography, digital subtraction radiography, and digital subtraction angiography. Computerized tomographic devices exist in virtually all hospitals, while the number of computerized two dimensional devices are rapidly growing. Because of its increased sensitivity to X-Rays, computerized X-Ray imaging systems can provide the advantage of a reduced dose of radiation to the patient, and/or a highly focused beam of radiation to the specific target organ of interest thereby avoiding undesirable exposure to other and possibly radiosensitive parts of the body, and/or the ability to accurately record images and data in coordination with organ motion using, for example, an electronic physiological trigger.

X-Ray based radiological imaging depends on the difference in attenuation or absorption of X-Rays by different types of tissue. Because of the high spatial resolution of two and three dimensional computerized X-Ray devices, images and data sets can rovide diagnostic information on smaller and more discrete sections of tissue. Because of the ability to obtain images and data sets at high speed unencumbered by the limitations imposed by the physics of isotope decay, two and three dimensional computerized X-Ray devices can generate more finite rate of flow and change in gas or blood distribution information and generate images with sharper edges due to less shadowing from organ/tissue movement. By itself, X-Ray radiology is used to image hard tissue such as bone, or, soft tissue, where there has been a change in structure due to disease or trauma which would change the density of the tissue. Examples of such medical applications are bone fractures, dead tissue and tumors of certain types at certain stages of their evolution. It is desirable to increase the contrast which can be attained between different types of soft tissue, an inside cavity and the soft tissue shaping that cavity, different soft tissue structures, and to evaluate the patency and condition of the arterio-venous system using X-Rays. To this end there have been developed certain contrast enhancement agents which are employed to increase the contrast and thus the quality of a radiological or X-Ray image.

Ionic and non-ionic iodine based X-Ray contrast enhancement agents are often used to better differentiate the arterio-venous system from the surrounding soft tissue and bone and to detect abnormalities in the arterio-venous system. Because iodine has a high atomic number, it absorbs or attenuates X-Rays in proportion to its presence. Iodine based contrast enhancement agents are injected intravenously and so their use involves an invasive procedure. The primary use of iodine based contrast agents is in the diagnosis of disease and appraisal of therapy concerning the arterio-venous system, which they improve the visualization of. Iodine based contrast enhancement agents stay in the vascular system unless the blood vessel is damaged by disease. They are also used to detect abnormalities within the blood vessels such as occlusions or aneurysms.

Because they are only vascular or fluid contrast agents, iodine based contrast agents cannot be used to detect and diagnose diseases in gas containing spaces such as those in the pulmonary system, involving obstructions of the tracheal-bronchial air passages, or non-functioning areas of the lungs where elasticity has been lost and gases are no longer readily exchanged during inhalation or exhalation as in emphyzema, or where the exchange of gases from the alveolar gas sacs in the lungs across the alveolar-capillary membrane into the blood and back again is not fully occuring, or if in a lung cancer patient whether ventilation is occurring in bullae which can lead to infection and other problems, or to assess what is the optimum gas mixture and pressure for respiratory therapy or ventilator support.

It is desirable to have a radiological imaging method that allows the performance of radiological imaging such as, for example pulmonary ventilation and bronchogram radiological imaging procedures by contrasting the internal gas filled compartments with the soft tissue that forms and also surrounds those gas compartments.

For this and other reasons, there has been developed a procedure using alternating breaths of stable xenon and oxygen, or the inhalation of a mixture containing a higher than atmospheric concentration of stable xenon with oxygen. The stable xenon is partially radiopaque to X-Rays due to its high atomic number and therefore attenuates or absorbs X-Rays in proportion to the concentration in areas of the body where X-Rays passed through a patient. Wherever the stable xenon is located, the absorption of X-Rays by the stable xenon makes that area appear, depending on the image recording or output device being used, either darker or lighter, or a different color, where the degree of darkness or lightness or color being a relative enhancement of the visual image and differentiation of one area from the other. The oxygen serves a life support function.

There are two major problems with the use of stable xenon in X-Ray contrast enhancement. One problem is the high cost of stable xenon. The other is that stable xenon is a relatively dense gas. At high concentrations it can potentially require greater effort by the well or ill patient for repeated respiration although not at a level placing the patient in distress or danger. This difficulty may be present to a greater degree in patients with pulmonary illnesses. Because of its density and the fact that a patient undergoing a pulmonary ventilation or bronchogram imaging procedure is in an upright position or supine position, stable xenon or a gas mixture containing a high concentration of stable xenon, tends to flow to the lowest area of the lungs due to gravity resulting in an uneven distribution of the stable xenon throughout the lungs and uneven exhalation that is not truly reflective of the patients pulmonary status, potentially negating the diagnostic value of a study. The result may be lowered contrast in upper areas of the tracheal-bronchial-alveolar gas space structures. While this may allow superior imaging of those portions of the gas spaces such as the bronchioles and alveoli that cannot be seen by other means due to the higher resolution of the computerized X-Ray systems, it could also provide an inferior or incomplete diagnostic assessment.

Accordingly, it is an object of this invention to provide an improved radiological imaging method which can provide improved contrast enhancement which may be especially suitable in computerized X-Ray radiological imaging procedures.

It is another object of this invention to provide an improved radiological imaging method wherein a contrast enhancement agent may be provided to a patient non-invasively, such as by inhalation, which can provide contrast enhancement that allows the performance of both bronchograms of the tracheal-bronchial gas space compartments extended to the smaller bronchioles, and pulmonary ventilation studies down to the level of the alveoli, using two or three dimensional computerized X-Ray imaging equipment.

The above and other objects which will become apparent to one skilled in the art upon a reading of this disclosure are attained by the present invention which is:

A method for carrying out radiological imaging of a patient comprising providing to the patient stable xenon, oxygen and helium and thereafter performing radiological imaging of the patient.

As used herein, the term "radiologic imaging" refers to either traditional X-Ray imaging where a patient is placed between an X-Ray source and a cassette containing a film screen and film, whereby the X-Rays reaching the film screen cause it to scintillate recording an image on the film, or "computerized X-Ray", imaging.

As used herein, the term "computerized X-Ray" means a process by which X-Rays are emitted by an X-Ray tube, go through a patient, are detected electronically, are stored in digital form, images are formed by software and displayed on a CRT and/or recorded in visual or digital form.

As used herein, the term "radiological contrast" or "contrast enhancement" means the property of being able to distinguish a compartment, organ, or tissue type of interest from others on a radiological image based on the degree of differentiation in the attenuation of X-Rays.

As used herein, the term "quantitative" means diagnostic information that can be expressed in numerical terms, describing the functionality or lack thereof of a specific organ or system in the body.

As used herein, the term "trachea" refers to the large gas passage outside the lungs.

As used herein, the term "bronchi" refers to the larger gas passages in the lung and "bronchiole" refers to the smaller gas passages in the lungs.

As used herein, "alveoli" refer to the gas sacs in the lung at the terminal end of the bronchioles, where gases are exchanged between the lung and the blood across what is referred to as the alveolar-capillary membrane, with oxygen entering the blood and being consumed in cellular metabolism, carbon dioxide being produced during cellular metabolism and exiting the blood back into the lung, and xenon crossing back and forth unchanged.

As used herein, the term "pulmonary ventilation" study means the evaluation of the capacity of the lungs to inhale and exhale, the distribution of gases in the lungs and the ability of the lungs to exchange gases with the blood via the alveolar-capillary membrane.

As used herein, "wash-in" refers to the inhalation of a gas mixture, during which the distribution and rate of distribution of the gas into the gas spaces/air passages is recorded.

As used herein, "equilibrium" refers to the point at which the diagnostic gas mixture which continues to be administered has fully distributed in the gas spaces to where it is going to go, or, if blood levels of the gas are being measured, the gas concentration in the blood has plateaued and approximately equals the concentration being administered.

As used herein, "washout" refers to the elimination and rate of elimination of a diagnostic gas mixture from the gas spaces and air passages after administration of the gas mixture has been ended.

As used herein, the term "bronchogram" means the evaluation of the trachea, large bronchi and smaller bronchiole gas passages in the lungs for obstructions and/or a reduction in the size of the air passages.

As used herein, the term "pulmonary angiogram" means the evaluation of the arteriovenous system in the lungs through the use of iodine based contrast enhancement using X-Ray based imaging systems.

As used herein, the term "cardiac angiogram" means the evaluation of the arteriovenous system going into and exiting the heart and including the flow of blood in the heart through the use of iodine based contrast enhancement using X-Ray based imaging systems.

As use herein, "CT" refers to a computerized three dimensional X-Ray imaging system which using an X-Ray source, detector, and specialized software, allows the accumulation, viewing and quantification of data in slices such that a specific area such as the entire chest, organ such as the lung, or compartment such as the bronchi in the lungs, may be viewed and analyzed either on a slice per slice basis, in sections combining several slices, or in its entirety using helical, spiral or volumetric continuous scanning and three dimensional reconstruction methods which allow the viewing of the target area at any level, depth or angle aspect.

As used herein, digital, radiography, digital fluoroscopy, digital subtraction fluoroscopy and digital subtraction angiography are high resolution two dimensional radiological imaging X-Ray systems which using an X-Ray source, detector, and specialized software, allow the two dimensional reconstruction of an image which can be stored in digital form, allowing for example the enlargement of a section for better diagnosis.

Subtraction capabilities allow, for example, the taking of an image without contrast enhancement of the anatomical fixed density bone and soft tissue, followed by taking an image after the administration of contrast enhancement of the target organ or compartment without moving the patient, whereby the first image can be substracted from the second, resulting in an image of the distribution of the contrast agent.

As used herein, the terms "renal blood flow" and "liver blood flow" refer to the imaging and quantification of the rate of blood flow into, within and out of the organs, to determine the patency of blood flow and organ function, whereby such information is of particular value in the determination of the need for a transplant, the selection of an organ for transplanting, and the evaluation of an organ after it is transplanted.

As used herein, the term "cerebral blood flow" refers to the flow of blood through the capillaries of the brain and across the blood brain barrier into brain cells, and which is reflective of which areas of the brain are receiving the required rate of flow to sustain the delivery of oxygen and nutrients for brain cell function, and where the visualization and quantification of cerebral blood flow is useful in evaluation of cerebrovascular diseases such as stroke, low blood flow also known as ischemia, trauma and brain death, and where xenon being soluble in blood plasma is a useful contrast enhancement agent for this purpose.

As used herein, the term "brain tissue function" refers to the relative functioning of normal and abnormal brain cells of the same type, of different types, and the determination of brain death, where the visualization of this function is useful in the evaluation of diseases such as epilepsy, ahlzeimers, and dementia, and where xenon is useful as a contrast agent because it is first soluble in blood plasma, second can cross the blood brain barrier mimicking the exchange of oxygen between the blood and brain cells, and third is soluble in lipids or fat, which is contained in different amounts by different types of brain tissue and in the same brain tissue dependent on how well those brain cells are functioning, where the degree of enhancement by stable xenon is therefore reflective of function.

As used herein, the term "non-invasive" means not requiring breaking the integrity of the body surface such as is required with an injection to administer a substance. Inhalation of a gas is considered to be a non-invasive procedure because the gas is inhaled during the normal act of breathing. Procedures that are invasive carry with them added risk of problems at the injection site and the breaking of the sterility of the arterio-venous system.

DETAILED DESCRIPTION

Figure 1:
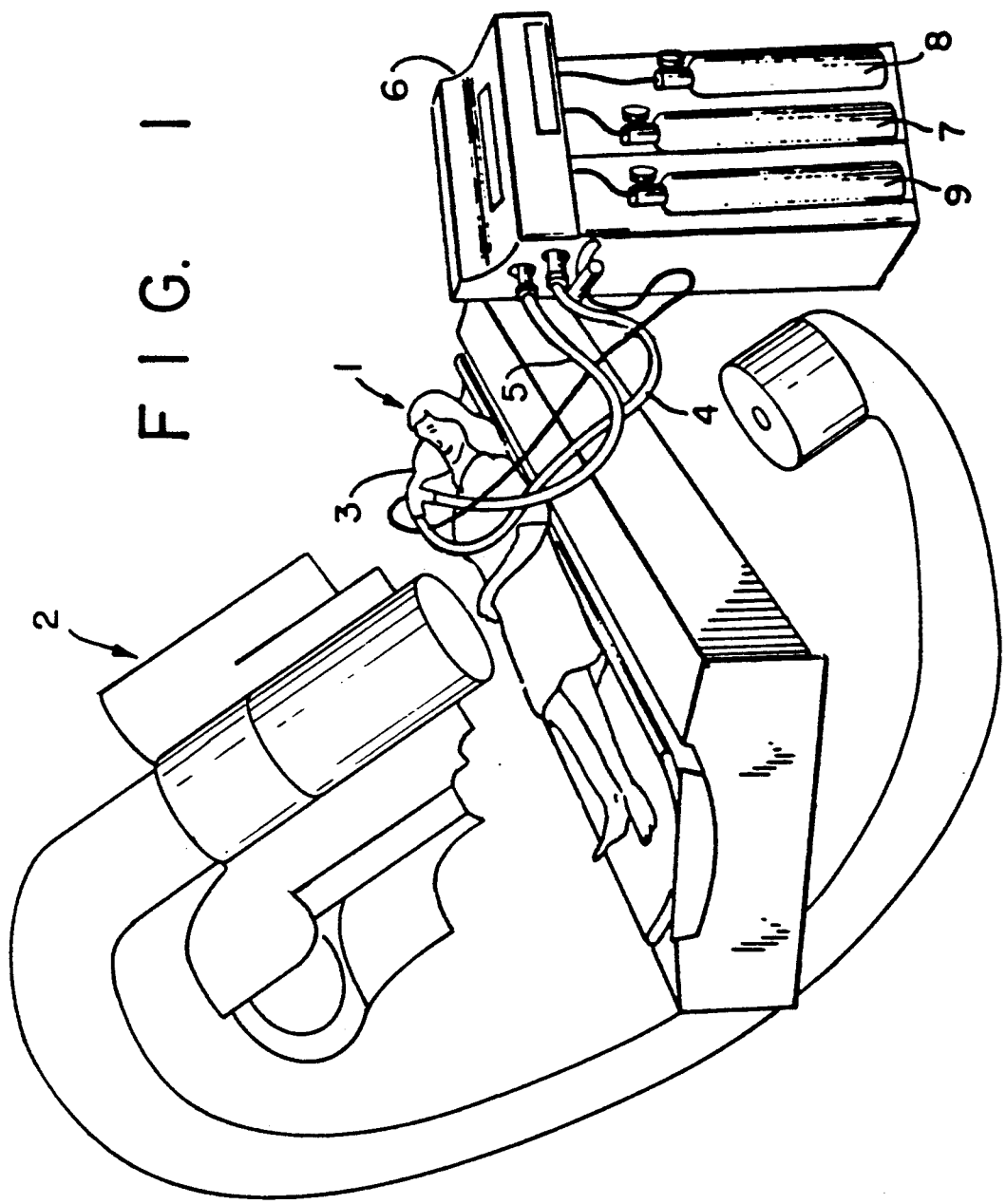
FIG. 1 is a representation of a human subject being given a gas mixture in the practice of the invention by a gas mixing or rebreathing delivery device and undergoing an examination with a two dimensional computerized X-Ray imaging system.

X-Ray radiological imaging takes advantage of the fact that certain structures within a body attenuate or absorb X-Rays to a greater degree than do other structures enabling an X-Ray image to show certain structures which could not otherwise be seen without surgery or an invasive procedure using a physical instrument, and to provide quantitative functional information based on the degree of contrast present. The X-Ray images show internal bone structures well, but provide poor images of soft tissue and gas filled areas. It is therefore difficult to distinguish different normal soft tissue areas from each other, and gas filled areas from soft tissue areas. An X-Ray image enhanced with iodine cannot be used to enhance gas filled areas. An X-Ray image by itself also cannot measure the dynamic distribution or exchange of gases in the structures of the lung, or of gases in and out of the blood within the body.

The invention is an improved method for carrying out radiological imaging of the gas spaces in the lung, the distribution and exchange of gases in the lung and the quantification of the distribution and exchange of gases in the lung. Furthermore, the invention is a novel way of producing images or data of a quality that reveal obstructions or constrictions of the tracheal air passage entering, and the bronchial air passages in, the lungs that are not otherwise obtainable by X-Ray radiological imaging procedures. The invention comprises in general the provision of helium along with stable xenon and oxygen to a patient, human or veterinary, while taking a radiological image and/or gathering radiological data using a computerized radiological imaging device. The stable xenon distributes throughout the gas passages of the lungs in direct correlation to the ability of gases to transit the gas passages freely, or where it is blocked by obstructions as in the case of chronic obstructive pulmonary diseases, or where the flow of gases are reduced due to constrictions as in the case of asthma as well as other disease states. The stable xenon also may remain trapped in the gas passages in direct correlation to the elasticity of the lungs, where such elasticity may be reduced and the xenon trapped as in the case of emphezema.

Wherever stable xenon flows, is present and/or trapped, it serves to absorb X-Rays in direct proportion to its presence. It thereby provides improved radiologic contrast. The degree of enhancement can be quantified pixel by pixel, or by voxels containing a number of pixels representing a volume of tissue, providing additional functional information by translation of the degree of contrast, and degree of contrast per unit time, to information that is of value in analyzing function. Stable xenon crosses the alveolar-capillary membrane into the vascular system and is returned to the lungs and exhaled unchanged by the body. Oxygen serves to sustain life. The helium serves to reduce the density of the gas, thereby providing a more uniform distribution of the stable xenon in the gas passages of the lungs with a patient in the upright or supine position and also reduces the work required for respiration by the patient. Helium is exhaled unchanged by the body.

In the case of renal blood flow, liver blood flow and cerebral blood flow, stable xenon which is soluble in blood plasma provides the contrast, which allows one to image and quantify the relative patency of the vascular system in the organ. This information is useful in the assessment of organs in patients potentially needing a liver or renal transplant, potential donor organs, and organs once they are transplanted, where there is potential risk of toxicity to or rejection of the existing or donor organ if iodine based contrast enhancement is used. In the case of cerebral blood flow and brain tissue function, stable xenon crosses the blood brain barrier during cerebral blood flow and being soluble in the lipids contained in the brain tissue, enhances brain tissue to different degrees dependent on the amount of cerebral blood flow, the specific type of brain tissue and the relative normal/abnormal state of the brain tissue. Both cerebral blood flow and brain tissue function assessment are useful in evaluation of cerebrovascular diseases such as stroke, occlusive vascular disease, aneurysm, ischemia, trauma, arteriovenous malformation, dementia, alzheimers and epilepsy. A stable xenon enhanced cerebral blood flow and brain tissue examination can be followed by an iodine contrast enhanced cerebral angiogram, which provides a high resolution image of the arterio-venous system in the brain.

The three gases, stable xenon, helium and oxygen may be administered to the patient separately, as a series of gas mixtures, or as a gas mixture containing all three components. When administered as a trigas mixture, the mixture comprises from 20 to 75.5 mole percent stable xenon, from 19.5 to 75.0 mole percent oxygen, and from 5.0 to 60.5 mole percent helium.

The gas mixture may also contain other components. For example in pulmonary ventilation studies, the gas mixture may also contain carbon dioxide which, if present, can be at a concentration of up to 10 mole percent for diagnostic purposes, preferably at a concentration within the range of from 1 mole percent to 7 mole percent. The carbon dioxide may be useful to evaluate the effect of carbon dioxide on respiration to determine the physiological response of the patient and/or to determine the effect of including carbon dioxide in a gas mixture for respiratory therapy. The gas mixture may also contain nitrogen, such as when the mixture is made up using air instead of oxygen. If present, nitrogen can be at a concentration of up to 55.5 mole percent. If air is used to make up the gas mixture, the mixture may have present other species in small amounts which may be found in air.

The three gases may be provided to the patient employing, for example, one of the following examination procedures.

Using two dimensional computerized X-Ray in the assessment of pulmonary ventilation;

(a) An imaging exam would be conducted without contrast, with the patient breatholding and the lungs in an inhaled position and/or exhaled position based on verbal command or an electronic or spirometric trigger linking the patient to the imaging system. This would be followed without changing the patient's position by an exam conducted with contrast enhancement, where for example;

(b) the patient undergoing a pulmonary ventilation study on a two dimensional computerized X-Ray system may inhale a mixture containing helium and oxygen alternated during routine breathing with either 100 percent stable xenon or a mixture of stable xenon and oxygen preferably being 70 percent to 80 percent stable xenon in oxygen, for a period of about 7–10 seconds, during which time data which comprises a set of dynamic images and quantitative data is acquired at rates of but not limited to 1 to 10 images per second, and where a respiratory trigger may be in use so that each set of images is taken at the end of inhalation and/or exhalation, or;

(c) the patient undergoing a pulmonary ventilation study on a three dimensional computerized X-Ray system such as a CT, HSCT or HRCT study may inhale a mixture containing stable xenon, helium and oxygen for several minutes during which imaging is continuous, or, a patient undergoing a helical, spiral or volumetric continuous scan on a CT may inhale the mixture for about 1.5 minutes followed by a breath hold of about 30 seconds or sufficient time to obtain an image, and;

(d) the option of (a) plus (b) or (c), followed by continuation of the imaging process to record the rate of elimination or washout of the stable xenon from the bronciole-alveolar gas space of the pulmonary system and the existance and distribution of stable xenon trapped in the gas spaces.

(e) The patient having a series of procedures as in (a) plus (b) or (c) and optionally (d), which in the case of two dimensional computerized X-Ray systems different aspects of the gas spaces of the broncial-alveolar gas space of the pulmonary system are studied such as posterior-anterior, left, right, and oblique views, and which in the case of three dimensional computerized X-Ray systems may be viewed from any angle aspect and any depth.

(f) The patient having one examination using one of the approaches above, followed by an examination in which a therapeutic amount of carbon dioxide or helium is delivered to the patient in mixture form, to compare and evaluate the physiological response to varying percentages of carbon dioxide or helium by the patient with the images and data obtained in the non-altered state, thereby potentially providing information of value in determining the impact of respiratory therapy gas mixtures containing carbon dioxide or helium in treating the patient's condition.

(g) The patient having one examination using one of the approaches above, followed by an examination in which the pressure of the gas mixture is changed, to compare and evaluate the physiological response to varying changes in gas delivery pressure by the patient with the images and data obtained in the non-altered state, thereby potentially providing information of value in determining the impact of different respiratory therapy pressures in treating the patient's condition.

(h) The manipulation of the data produced above so that any of the plain and stable xenon enhanced images can be compared to or subtracted from each other, singley or in combination, and where the subtraction of the plain X-Ray image and data from the stable xenon enhanced images and data eliminates most of the soft tissue image and artifact, providing a clearer depiction of the air passages based on the xenon contained therein.

(i) The manipulation of the data produced above so that the rate of flow in and out of the lungs of stable xenon can be quantitatively determined.

(j) The quantification of densitometry across the lung to determine the existance and measure local defects in ventilation based on high resolution images, and the ability to add xenon enhanced images taken in the same position and registered with each other, thereby increasing the statistical relevance of the interpretation.

Using two dimensional computerized X-Ray in a bronchogram procedure, the patient may undergo at the physician's option and dependent on the imaging system used one or more of the same procedures described above, including the evaluation of therapeutic pharmaceuticals such as bronchiodilators.

Using two dimensional computerized X-Ray in the assessment of chest pain, all or parts of procedure described above for pulmonary ventilation may be conducted, followed by a cardiac angiogram and/or pulmonary angiogram using ionic or non-ionic iodine contrast enhancement agents, with the resulting images and sets of data being directly and anatomically coupled to and correlatable with each other.

Using two dimensional computerized X-Ray in the assessment of renal or liver blood flow examinations, the patient would be positioned to image the target organ and an exam conducted without contrast enhancement. The gas mixture would be administered to the patient in sufficient concentration of stable xenon and for a sufficient length of time to acheive the contrast level and therefore image quality and statistical relevance desired. Stable xenon enhanced images and data would be recorded, either at fixed points of time, or after maximum concentration had been achieved. The X-Ray image and data recorded without stable xenon enhancement would be subtracted from the stable xenon enhanced image data, thereby removing soft tissue and bone densities from the image and data set. Areas of normal, to high, to low or no blood flow would then be identifiable and quantifiable. About 20 minutes after conducting a stable xenon enhanced examination, an iodine contrast enhanced exam of the arteriovenous system in the target organ could be conducted, resulting in a plain X-Ray image, and a xenon enhanced, and an iodine enhanced X-Ray image of the target organ, all of which are in perfect registration with each other, and may be subtracted from each other to potentially improve diagnosis.

Using three dimensional X-Ray in the evaluation of the trachea-bronchi-alveolar gas spaces in the lungs and pulmonary ventilation there is performed an exam without contrast with the patient breath holding in one of several imaging modes, including but not limited to slice by slice; and/or helical, spiral or volumetric continous scanning such that a three dimensional reconstruction of the entire trachea-bronchi-alveolar gas space and lungs can be generated; followed by, for example, the patient being allowed to breathe a mixture of 30-40 percent stable xenon with helium and oxygen for about 1.5 minutes, followed by an exam being performed using the same imaging mode with the patient then breath holding at inhalation about 30 seconds or for a sufficient time to obtain an image in that mode. This is followed by the subtraction of the first from the second image and data set obtained, resulting in a data set reflecting the distribution of the stable xenon in the gas spaces which can be both viewed at any depth and from any aspect angle in three dimensions, compared directly against anatomy using the image taken without contrast enhancement, and where the rate of distribution and degree of distribution of stable xenon gas in tracheabronchi-alveoli gas spaces and the pulmonary ventilation process itself can be quantified. These procedures may be carried out with the patient continuously breathing a gas mixture of stable xenon, helium and oxygen and individual slices or specific depths being evaluated during washin and/or equilibrium and/or washout by rapid scanning using for example high speed CT.

Using three dimensional X-Ray in the evaluation of cerebral blood flow and brain tissue function using specialized software, where images and data sets are obtained at slices or levels of the brain without contrast, followed by the inhalation of a mixture of for example 26 to 33 percent stable xenon, helium and oxygen which is inhaled until the concentration of stable xenon in the blood is in equilibrium with the concentration being adminstered, at which time a second set of images and data sets are obtained. The non contrast enhanced image and data sets are subtracted from the enhanced image and data sets, resulting in an image and data set representing the distribution of stable xenon, which can be used to calculate local cerebral blood flow (CBF) and brain tissue function, based on the pharmacology of stable xenon. This process provides high resolution local CBF information that directly correlates to anatomy, allows one to rapidly repeat CBF studies to determine the effect of pharmaceutical therapy, allows one to challenge existing physiology, and allows one to perform an iodine contrast enhanced exam of the arterio-venous system within 20 minutes of ending the stable xenon enhanced exam.

The mixture containing stable xenon, helium and oxygen or air may be administered directly from a single cylinder or tank, or one or a plurality of cylinders or tanks by a delivery device that mixes the gases to the required concentrations and allows the exhaled gases to escape, or recycles the exhaled gases in a rebreathing system thereby reducing the cost per examination.

Monitors may also be placed in the mouthpiece or facemask to monitor the percent of each gas exhaled per exhalation, to obtain physiological information of added diagnostic value.

In pulmonary ventilation examinations, the approach using alternate breathing of gases with a two dimensional computerized X-Ray system or high speed CT that allows very rapid imaging, may be performed using a cylinder or tank containing pre-mixed helium and oxygen and a cylinder or tank containing 100 percent stable xenon or 80 percent stable xenon in oxygen, delivered via a device that allows the switching from one to the other, breath to breath, on an automatic basis using a spirometric or other type of physiological trigger or manually controlled basis so that images are obtained at full inspiration or exhalation with minimal movement.

Among the many radiological imaging procedures which may be employed in the practice of this invention are pulmonary ventilation imaging for chronic obstructive pulmonary diseases, pulmonary ventilation imaging for emphyzema, bronchograms for asthma, and a combination of the plain chest X-Ray procedure, the pulmonary ventilation and the iodine contrast enhanced pulmonary angiogram to evaluate suspected pulmonary embolism, a stable xenon enhanced pulmonary ventilation procedure and iodine enhanced cardiac angiogram to rule out causes of chest pain; liver, renal and cerebral blood flow imaging and quantitative measurement; and brain tissue function imaging and quantitative measurement.

FIG. 1 illustrates the use of the invention in connection with a two dimensional computerized X-Ray system for pulmonary ventilation imaging. Referring to FIG. 1 there is illustrated a human patient 1 on the imaging table of a digital radiography or DR unit 2. The gas mixture of this invention is administered to patient 1 through face mask 3 into which gas flows through line 4 and out from which exhalant flows through line 5. The gas mixture is made up by mechanical gas mixing device 6 which takes gas components from one or more cylinders or tanks. In FIG. 1, there are illustrated three such cylinders 7, 8 and 9. For example, cylinder 7 may contain stable xenon, cylinder 8 may contain helium and cylinder 9 may contain oxygen. The ventilation study generates both a qualitative image and quantitative data for diagnostic use, with very high resolution that allows the detection of defects in very small lung regions.

Figure 2:
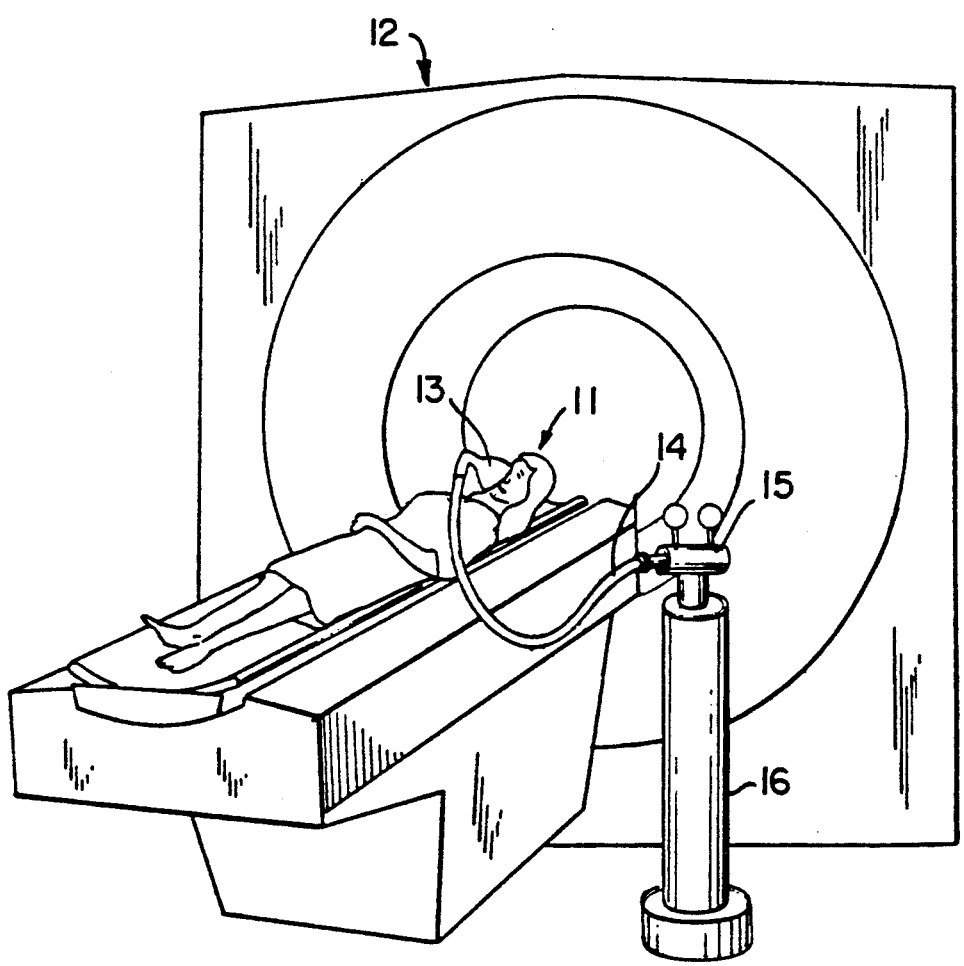
FIG. 2 is a representation of a human subject being given a gas mixture in the practice of the invention from a single pre-mixed cylinder and undergoing an examination with a three dimensional computerized X-Ray imaging system.

FIG. 2 illustrates the use of the invention in connection with a three dimensional computerized X-Ray system. Referring to FIG. 2 there is illustrated a human patient 11 about to enter a computerized tomographic or CT unit 12. The gas mixture of this invention is administered to patient 11 through face mask 13 into which gas flows through line 14 originating from a one or two stage gas pressure regulator 15, which is on a cylinder 16 containing the gas mixture pre-prepared and filled at the manufacturer's production facility. When used with helical, spiral or volumetric continous scanning techniques on a CT, a reconstructed three dimensional data set of the trachea, bronchi, bronchioles and pulmonary ventilation distribution can be obtained providing a qualitative image and allowing quantitative measurement of gas distribution with very high resolution, that allows examination of all or part of the gas passages at any depth and/or angle aspect.

It is further desireable to be able to further enhance differences between soft tissue and bone, and the gas containing compartments of the trachea, bronchi and alveoli, by subtracting the baseline fixed tissue data and densities generated by the regular X-Ray imaging of soft and bone tissue anatomy from the contrast improving the even distribution of stable xenon while the patient is in a supine or upright position thereby providing a diagnostic image and data set more relevant to the patients condition and therefore of greater diagnostic value. This provides the ability to perform X-Ray diagnostic evaluations of the gas space and ventilatory physiology of the pulmonary organ system which cannot be performed with iodine based contrast enhancement agents and also provides the ability to generate using two or three dimensional X-Ray systems, high spatial resolution images and quantitative information concerning the gas spaces and passages including the trachea, bronchi, bronchioles, alveoli and pulmonary ventilation function that can be directly correlated to anatomy, on a basis which are unobtainable by any other enhanced or non-enhanced X-Ray, or, any Nuclear Medicine radiological imaging procedure using gases. In addition, it allows, because of the fast imaging time of 2 dimensional computerized digital radiographic, digital subtraction radiographic and digital subtraction angiographic imaging devices, and three dimensional high speed computerized tomography, the acquisition of images and sets of data each consisting of less then one second duration, allowing visualization and quantification of the flow of the subject invention contrast enhancement agent into and out of the air passages of the lungs in time elements and with a degree of high resolution unobtainable with nuclear medicine procedures.

Those skilled in the art will recognize that although the invention has been described in detail with reference to certain specific embodiments, there are other embodiments of the invention within the spirit and scope of the claims.

I claim:

1. A method for carrying out radiological imaging of a patient comprising providing to the patient three gas components stable xenon, oxygen and helium either separately, as a series of gas mixtures, or as a gas mixture containing all three gas components and thereafter performing radiological imaging of the patient.

2. The method of claim 1 where in the stable xenon, oxygen and helium are separately contained and provided in series to the patient.

3. The method of claim 1 wherein a mixture comprising stable xenon and oxygen is first provided to the patient and a mixture comprising helium and oxygen is provided second to the patient prior to the radiological imaging.

4. The method of claim 1 wherein a mixture comprising helium and oxygen is first provided to the patient and a mixture comprising stable xenon and oxygen is provided second to the patient prior to the radiological imaging.

5. The method of claim 1 wherein a combination of a therapeutic gas mixture containing helium at a specific pressure is provided to a patient, followed by or alternated with the patient being provided with a gas mixture containing stable xenon and oxygen.

6. The method of claim 1 wherein a combination of a therapeutic gas mixture containing carbon dioxide at a specific pressure is provided to a patient, followed by or alternated with the patient being provided with a gas mixture containing stable xenon, oxygen and helium.

7. The method of claim 1 wherein the stable xenon, oxygen and helium are provided to the patient as a gas mixture comprising:
   (A) from 20.0 to 75.5 mole percent stable xenon;
   (B) from 19.5 to 75.0 mole percent oxygen; and
   (C) from 5.0 to 60.5 mole percent helium.

8. The method of claim 7 wherein the gas mixture further comprises carbon dioxide in a concentration of up to 10 mole percent.

9. The method of claim 7 wherein the gas mixture further comprises nitrogen in a concentration of up to 55.5 mole percent.

10. The method of claim 1 wherein the three gas components further comprises carbon dioxide.

11. The method of claim 1 further comprising taking a baseline radiological image of the patient prior to providing the stable xenon, oxygen and helium to the patient and subtracting the baseline radiological image from a radiological image taken after the provision of stable xenon, oxygen and helium thereby generating an improved image and set of data.

12. The method of claim 1 wherein the three gas components further comprise nitrogen.

13. The method of claim 1 wherein the stable xenon, oxygen and helium are inhaled by the patient prior to the radiological imaging.

* * * * *